(12) United States Patent
Siber et al.

(10) Patent No.: US 6,602,470 B2
(45) Date of Patent: Aug. 5, 2003

(54) OPTICAL SENSOR AND METHOD FOR PRODUCING SAME

(75) Inventors: Bernd Siber, Glonn (DE); Thomas Brinz, Bissingen Unter der Teck (DE); Heidrun Potthast, Gerlingen (DE); Andreas Hensel, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/861,917

(22) Filed: May 21, 2001

(65) Prior Publication Data
US 2002/0012612 A1 Jan. 31, 2002

(30) Foreign Application Priority Data
May 20, 2000 (DE) .......................... 100 25 097

(51) Int. Cl.[7] .............................. G01N 21/78
(52) U.S. Cl. ............... 422/82.09; 436/134; 436/167
(58) Field of Search ................. 436/134, 164, 436/166, 167; 422/56, 57, 82.05, 82.09; 427/164, 165

(56) References Cited

U.S. PATENT DOCUMENTS

| | | | | |
|---|---|---|---|---|
| 3,823,529 A | * | 7/1974 | Hughes et al. | 95/44 |
| 4,043,934 A | * | 8/1977 | Shuler et al. | 252/186.33 |
| 4,508,694 A | * | 4/1985 | Doyle et al. | 423/246 |
| 5,280,548 A | * | 1/1994 | Atwater et al. | 385/12 |
| 5,405,583 A | * | 4/1995 | Goswami et al. | 422/82.05 |
| 5,618,493 A | | 4/1997 | Goldstein et al. | |
| 5,733,505 A | * | 3/1998 | Goldstein et al. | 422/83 |
| 5,998,594 A | * | 12/1999 | Goodman et al. | 536/1.11 |

FOREIGN PATENT DOCUMENTS

GB    2368394    *  5/2002

* cited by examiner

Primary Examiner—Jeffrey Snay
(74) Attorney, Agent, or Firm—Kenyon & Kenyon

(57) ABSTRACT

An optical sensor is described for determining the concentration of a gas in gas mixtures, which can especially be used for determining the carbon monoxide content of the air. It includes a radiation source, a sensitive layer positioned on a translucent substrate, and a detector. The sensitive layer of the sensor contains a transition metal compound which forms a transition metal complex with the gas to be determined.

15 Claims, 1 Drawing Sheet

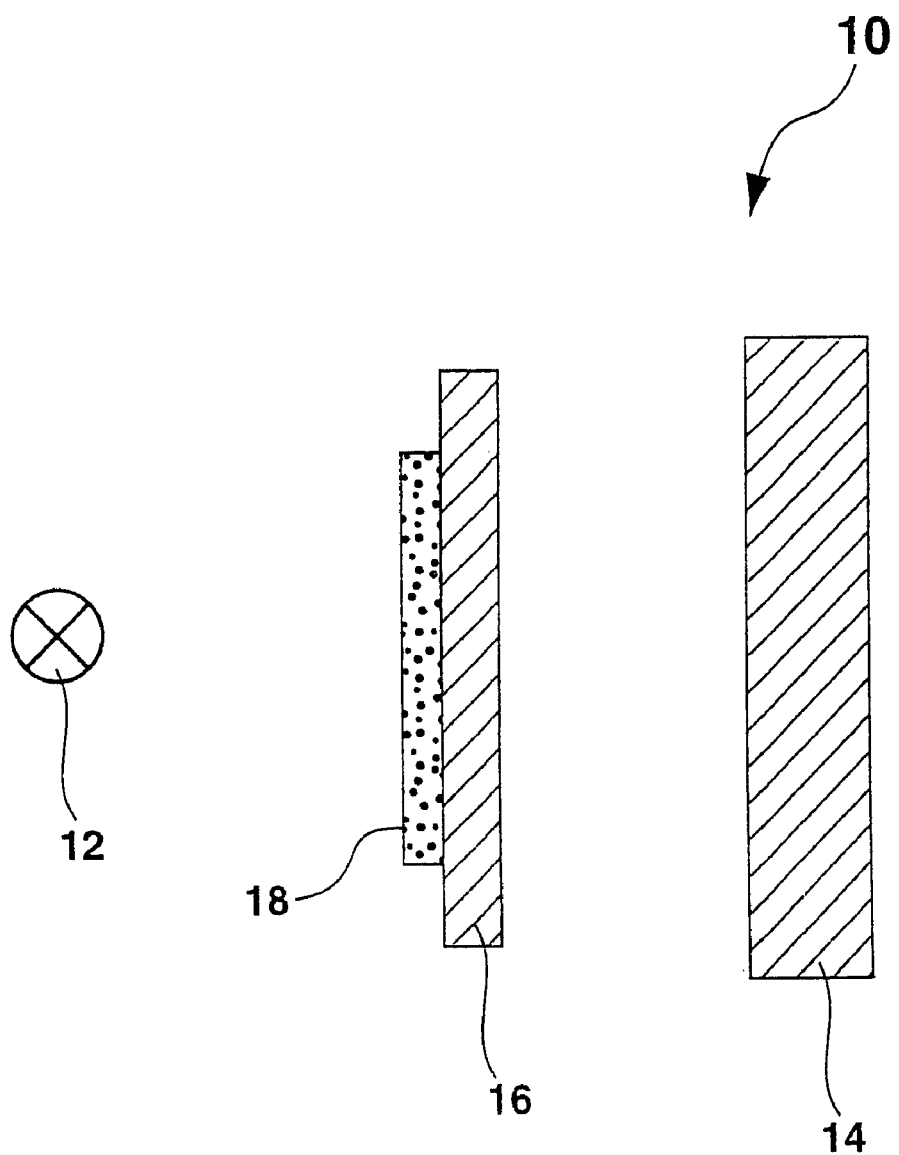

OPTICAL SENSOR AND METHOD FOR PRODUCING SAME

FIELD OF THE INVENTION

The present invention relates to an optical sensor as well as a method for producing the same, and its use.

BACKGROUND INFORMATION

Optical sensors for determining the carbon monoxide content in the air are used, among other things, in fire alarms. Their function is based on the fact that a layer sensitive to carbon monoxide changes color reversibly upon contact with the gas to be ascertained. This change of color is recorded by a detector, and when a predetermined minimum concentration is exceeded, an alarm is triggered.

In U.S. Pat. No. 5,618,493 such a carbon monoxide sensor is described. It includes two substrates to which sensitive layers are applied. One of the layers is provided especially for low humidity and low air temperature, the other for a higher temperature and humidity. In order to be able to detect the color change of the sensitive layers at contact with carbon monoxide, a light-emitting diode is provided as radiation source in the fire alarm described, whose light passes through the sensitive layers. The absorption appearing during this process is ascertained, using a photodiode. However, such a sensor does not have the sensitivity suited to strict standards, and has a long response time.

The present invention is based on the object of making available a carbon monoxide sensor having great sensitivity and a short response time.

SUMMARY OF THE INVENTION

The optical sensor according to the present invention has the advantage that it has a very short response time and very high sensitivity to carbon monoxide. This is achieved by adding a transition metal compound to the sensitive layer of the sensor, which reversibly undergoes chemical bonding with CO, and thus actively brings carbon monoxide in the air to the sensitive layer. This makes possible the rapid reaction of the sensor to changing carbon monoxide concentrations, but also a lowering of the response threshold of the sensitive layer. The sensitive layer is preferably deposited as a thin film on a translucent substrate.

As a transition metal compound, copper(I) chloride is suitable above all, since it rapidly and effectively forms complexes with carbon dioxide at room temperature.

In a particularly advantageous embodiment, the sensitive layer includes a matrix of hydrogel, since carbon monoxide has a substantially higher diffusion constant and solubility in aqueous media than in the usual polymer layers. This further raises the sensitivity and lowers the response time.

BRIEF DESCRIPTION OF THE DRAWING

The FIGURE shows a schematic representation of an exemplary embodiment of the optical sensor according to the present invention.

DETAILED DESCRIPTION

The optical sensor 10 illustrated in the FIGURE contains a radiation source 12 which may be such as a light-emitting diode, and a detector 14 which is developed, for example, as a photodiode. Between the radiation source 12 and the detector 14 a translucent substrate 16 is positioned. For the material of the translucent substrate 16, other optically transparent substances such as polymethacrylates can be used.

On the substrate 16 there is a sensitive layer 18, which reversibly changes its color when a minimum concentration of carbon monoxide is exceeded. The sensitive layer 18 includes a matrix in which there are the compounds responsible for the sensitivity of the sensor. In a preferred embodiment of the sensitive layer 18, this matrix is made of a hydrogel, but other polymers are also suitable, such as PVC and ethylcellulose. The use of hydrogel as matrix simplifies the production of the sensitive layer, since the substances further provided in the sensitive layer are predominantly water soluble metal salts, and, because of the water content of the hydrogel, they distribute themselves in it very homogeneously in dissolved form.

Beyond that, the sensitive layer 18 demonstrates a very good response to carbon monoxide when a hydrogel is used as matrix, since the diffusion constant and the solubility of CO in water are substantially higher than in the usual polymers.

In order to deliver the carbon monoxide present in the air as rapidly as possible, and in sufficient quantity to the sensitive layer 18, the latter preferably contains a transition metal compound which reversibly forms so-called carbonyl complexes with carbon monoxide, rapidly and with high yield. Suitable for this are compounds of the transition metals manganese, rhenium or iron (II), as well as the halides of rhodium, iridium and copper (I). The use of copper(I) chloride is especially preferred.

Besides a transition metal compound for the improved take-up of carbon monoxide into the sensitive layer 18, the latter contains further substances used for detecting the carbon monoxide content of the air. These may be divided into three groups. Specifically, these are palladium salts as redox catalysts, molybdenum compounds as redox indicators, whose color change indicates the presence of carbon monoxide, and copper(II) compounds to guarantee the reversibility of the color change.

In general, as the palladium salts, all water soluble salts of bivalent palladium can be used which are able to catalyze the reaction from CO to $CO_2$ This applies above all to palladium halides. During the oxidation of carbon monoxide to carbon dioxide the bivalent palladium goes over into an oxidation state of 0.

Palladium in oxidation state 0 is in a position to reduce a molybdenum(VI) compound which is also contained in the sensitive layer. As molybdenum compound, for example, molybdoorthosilicic acid, $H_4[Si(Mo_3O_{10})_4]*xH_2O$ is used. In this process, the molybdenum goes over into oxidation state +III, and the compound shows a color change from yellow to blue. This is detected by an absorption or transmission measurement in the wavelength range from 500 to 1100 nm.

To guarantee the reversibility of the color change, the sensitive layer 18 also contains a copper(II) compound, such as copper sulfate or a copper(II) halide. The molybdenum (III) compounds formed during the color reaction are returned to the hexavalent state by the $Cu^{2+}$.

The $Cu^+$ thus formed is reoxidized to $Cu^{2+}$ by such as the oxygen in the air. The backward reaction of the color change as well as the regeneration of the copper(II) compound take longer than the reactions leading to the color change. That is why the color change of the molybdenum compound is detectable at all.

In order to make the gas permeability of the sensitive layer 18 as great as possible, a softening agent is also added to the layer. As softening agent, bis-(2-ethylhexyl)sebacate is preferably used.

During the production of the optical sensor, a solution of the metal salts, the hydrogel or polymers, and the softening agent in water or tetrahydrofuran are applied and dried. Films are produced thereby, which advantageously have a thickness of 10 to 20 μm.

The present invention is not limited to the exemplary embodiment described, but rather, in addition to the optical sensor for determining carbon monoxide, further applications can be imagined, in which a transition metal compound is used to form complexes for the improvement of the sensitivity of a gas sensor. This would apply, for instance, to the detection of hydrogen cyanide gas.

What is claimed is:

1. An optical sensor for determining a concentration of a gas in a gas mixture, comprising:
    a radiation source;
    a detector;
    a translucent substrate arranged between the radiation source and the detector; and
    a sensitive layer positioned on the translucent substrate and containing a transition metal compound that forms a transition metal complex with the gas, the sensitive layer including a material capable of causing the sensitive layer to change color.

2. The optical sensor according to claim 1, wherein:
    the gas includes carbon monoxide, and
    the gas mixture includes air.

3. The sensor according to claim 1, wherein:
    the gas includes carbon monoxide.

4. The sensor according to claim 1, wherein:
    the transition metal compound includes one of Mn, Re, and Fe(II) as a transition metal.

5. The sensor according to claim 1, wherein:
    the transition metal compound includes a halide of a transition metal including one of Rh, Ir, and Cu(I).

6. The sensor according to claim 5, wherein:
    the transition metal compound includes copper(I) chloride.

7. The sensor according to claim 1, wherein:
    the sensitive layer includes at least one of a compound of bivalent palladium, a compound of molybdenum, and a compound of copper(II).

8. The sensor according to claim 7, wherein:
    the compound of bivalent palladium includes a palladium halide.

9. The sensor according to claim 7, wherein:
    the molybdenum compound includes a molybdoorthosilicic acid having the empirical formula $H_4[Si(Mo_3O_{10})_4] \cdot xH_2O.$ 10. The sensor according to claim 1, wherein:
    the sensitive layer includes a polymer matrix.

11. The sensor according to claim 10, wherein:
    the polymer matrix includes a hydrogel.

12. The sensor according to claim 1, wherein:
    the sensitive layer includes a softening agent.

13. A method, comprising:
    producing a sensitive layer in the form of a thin film by applying a solution of hydrogel, a softening agent, and metal salts to a translucent substrate and by performing a subsequent drying process, in order to produce a sensor that includes:
        the translucent substrate, and
        the sensitive layer positioned on the translucent substrate and containing a transition metal compound that forms a transition metal complex with a gas, the sensitive layer including a material capable of causing the sensitive layer to change color.

14. The method according to claim 13, wherein:
    the thin film has a thickness of 10 to 20 μm.

15. The method according to claim 13, wherein:
    the solution includes tetrahydrofuran as a solvent.

* * * * *

UNITED STATES PATENT AND TRADEMARK OFFICE
CERTIFICATE OF CORRECTION

PATENT NO. : 6,602,470 B2
DATED : August 5, 2003
INVENTOR(S) : Siber et al.

It is certified that error appears in the above-identified patent and that said Letters Patent is hereby corrected as shown below:

<u>Column 4,</u>
Line 5, delete "at least one of"

Signed and Sealed this

Twenty-fifth Day of May, 2004

JON W. DUDAS
*Acting Director of the United States Patent and Trademark Office*